(12) United States Patent
Fowler et al.

(10) Patent No.: US 8,096,941 B2
(45) Date of Patent: Jan. 17, 2012

(54) INSERTABLE DEVICE AND SYSTEM FOR MINIMAL ACCESS PROCEDURE

(75) Inventors: Dennis L. Fowler, New York, NY (US); Peter K. Allen, Pleasantville, NY (US); Andrew T. Miller, Brooklyn, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 944 days.

(21) Appl. No.: 11/474,061

(22) Filed: Jun. 23, 2006

(65) Prior Publication Data

US 2007/0032700 A1   Feb. 8, 2007

Related U.S. Application Data

(63) Continuation of application No. 10/620,298, filed on Jul. 15, 2003, now Pat. No. 7,066,879.

(51) Int. Cl.
*A61B 1/00* (2006.01)

(52) U.S. Cl. ........ 600/102; 600/109; 600/114; 600/160; 600/173

(58) Field of Classification Search .................. 600/109, 600/114, 160, 173
See application file for complete search history.

(56) References Cited

U.S. PATENT DOCUMENTS

| | | | | |
|---|---|---|---|---|
| 3,643,653 A * | 2/1972 | Takahashi et al. | ............ | 600/129 |
| 4,040,413 A * | 8/1977 | Ohshiro | ........................ | 600/116 |
| 4,402,311 A * | 9/1983 | Hattori | ........................... | 600/117 |
| 4,651,201 A | 3/1987 | Schoolman | | |
| 5,166,787 A * | 11/1992 | Irion | .............................. | 348/75 |
| 5,604,531 A | 2/1997 | Iddan et al. | | |
| 5,653,677 A * | 8/1997 | Okada et al. | .................. | 600/112 |
| 5,976,076 A | 11/1999 | Kolff et al. | | |
| 6,162,171 A * | 12/2000 | Ng et al. | ........................ | 600/141 |
| 6,240,312 B1 * | 5/2001 | Alfano et al. | ................. | 600/476 |
| 6,352,503 B1 * | 3/2002 | Matsui et al. | ................. | 600/104 |
| 6,428,469 B1 | 8/2002 | Iddan et al. | | |
| 6,454,727 B1 | 9/2002 | Burbank et al. | | |
| 6,527,753 B2 * | 3/2003 | Sekine et al. | ................. | 604/264 |
| 6,540,693 B2 | 4/2003 | Burbank et al. | | |
| 6,648,817 B2 | 11/2003 | Schara et al. | | |
| 6,719,684 B2 | 4/2004 | Kim et al. | | |

(Continued)

FOREIGN PATENT DOCUMENTS

JP           60-232524           11/1985

(Continued)

OTHER PUBLICATIONS

M2A™ Capsule Endoscopy, M. Yu, Gastroenterology Nursing, vol. 25, No. 1, 2001, pp. 24-27.

(Continued)

*Primary Examiner* — Matthew J Kasztejna
(74) *Attorney, Agent, or Firm* — Kenyon & Kenyon LLP

(57) ABSTRACT

The present invention provides a system and single or multi-functional element device that can be inserted and temporarily placed or implanted into a structure having a lumen or hollow space, such as a subject's abdominal cavity to provide therewith access to the site of interest in connection with minimally invasive surgical procedures. The insertable device may be configured such that the functional elements have various degrees of freedom of movement with respect to orienting the functional elements or elements to provide access to the site from multiple and different orientations/perspectives as the procedure dictates, e.g., to provide multiple selectable views of the site, and may provide a stereoscopic view of the site of interest.

16 Claims, 6 Drawing Sheets

U.S. PATENT DOCUMENTS

| | | | |
|---|---|---|---|
| 6,726,675 B1 * | 4/2004 | Beyar | 604/510 |
| 6,916,286 B2 * | 7/2005 | Kazakevich | 600/173 |
| 6,951,536 B2 * | 10/2005 | Yokoi et al. | 600/128 |
| 7,066,879 B2 | 6/2006 | Fowler et al. | |
| 7,322,934 B2 * | 1/2008 | Miyake et al. | 600/173 |
| 7,511,733 B2 * | 3/2009 | Takizawa et al. | 348/68 |
| 2001/0051766 A1 * | 12/2001 | Gazdzinski | 600/309 |
| 2002/0042562 A1 * | 4/2002 | Meron et al. | 600/361 |
| 2002/0198470 A1 | 12/2002 | Imran et al. | |
| 2003/0032863 A1 | 2/2003 | Kazakevich | |
| 2003/0092964 A1 | 5/2003 | Kim et al. | |
| 2003/0092966 A1 | 5/2003 | Schara et al. | |
| 2004/0138529 A1 * | 7/2004 | Wiltshire et al. | 600/144 |
| 2005/0234296 A1 * | 10/2005 | Saadat et al. | 600/129 |

FOREIGN PATENT DOCUMENTS

| | | |
|---|---|---|
| JP | 2000175865 | 6/2000 |
| JP | 2002-334761 | 11/2002 |

OTHER PUBLICATIONS

A Compact, Compliant Laparoscopic Endoscope Manipulator, P. Berkelman et al., 2002 IEEE, pp. 1870-1875.

Alignment Using an Uncalibrated Camera System, B.H. Yoshimi et al., 1995 IEEE, pp. 516-521.

Computing Camera Viewpoints in an Active Robot Work Cell, S. Abrams et al., The Int'l. Journal of Robotics Research, vol. 18, No. 3, 1999, pp. 267-285.

The Intuitive™ Telesurgery System: Overview and Application, G.S. Guthart et al., 2000 IEEE, pp. 618-621.

Visual Servoing by Partitioning Degrees of Freedom, P.Y. Oh et al., 2001 IEEE, pp. 1-17.

Comparison of Laparoscopic Imaging Systems and Conditions Using a Knot-Tying Task, F. Tendick et al., Computer Aided Surgery, 1997, pp. 24-33.

RealTime Tracking Meets Online Grasp Planning, D. Kragić et al., 2001 IEEE, pp. 2460-2465.

Biomedical Micro Robots Driven by Miniature Cybernetic Actuator, K. Ikuta et al., 1994 IEEE, pp. 263-268.

Constraint-Based Sensor Planning for Scene Modeling, M.K. Reed et al., 2000 IEEE, pp. 1460-1467.

Micro Motor Based A New Type of Endoscope, L.M. Gao et al., 1998 IEEE, pp. 1822-1825.

Robotic Arm Enhancement to Accommodate Improved Efficiency and Decreased Resource Utilization in Complex Minimally Invasive Surgical Procedures, W.P. Geis et al., http://www.ittc.ukans.edu/~sgauch/767/files/076.html, 1996, pp. 1-6.

* cited by examiner

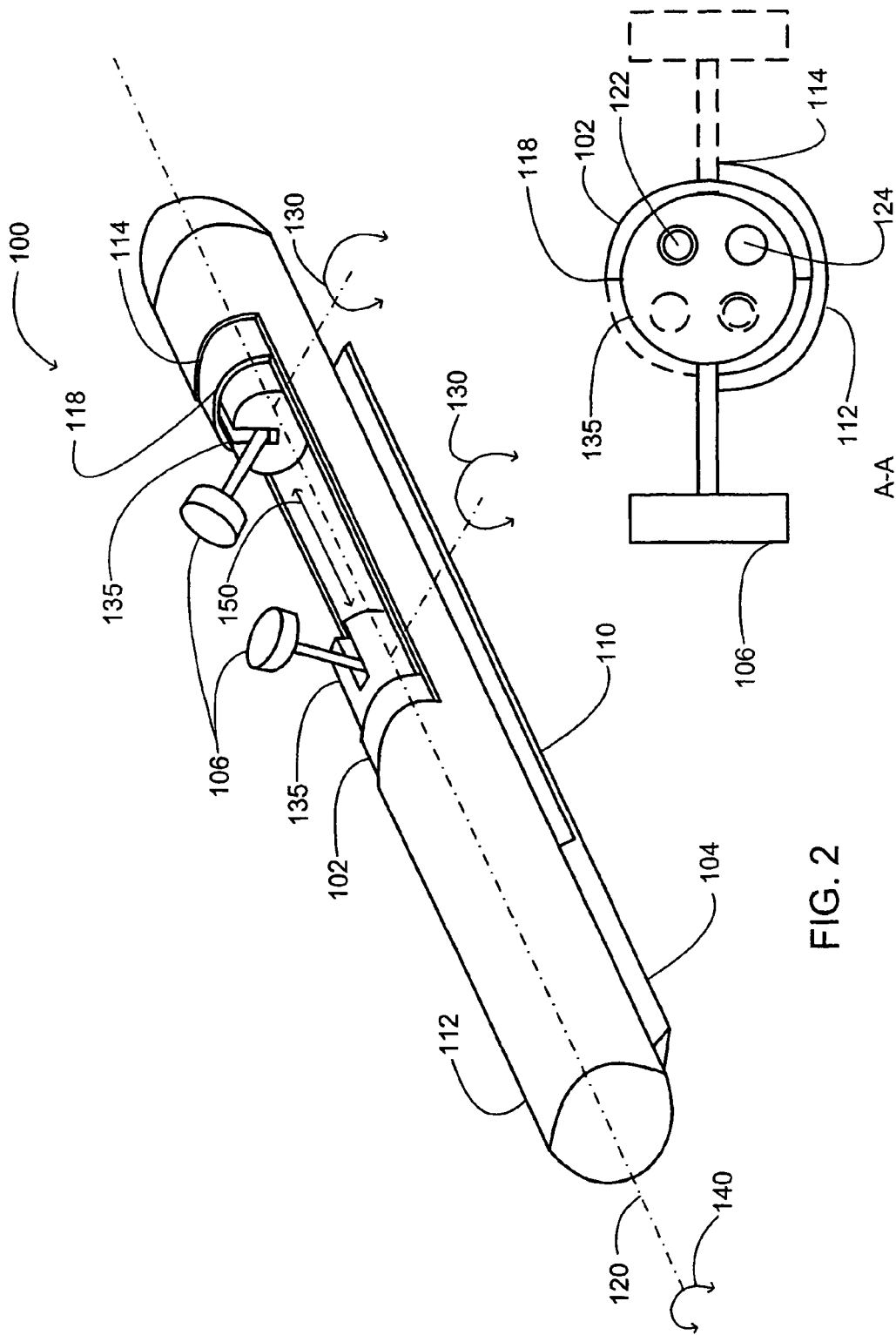

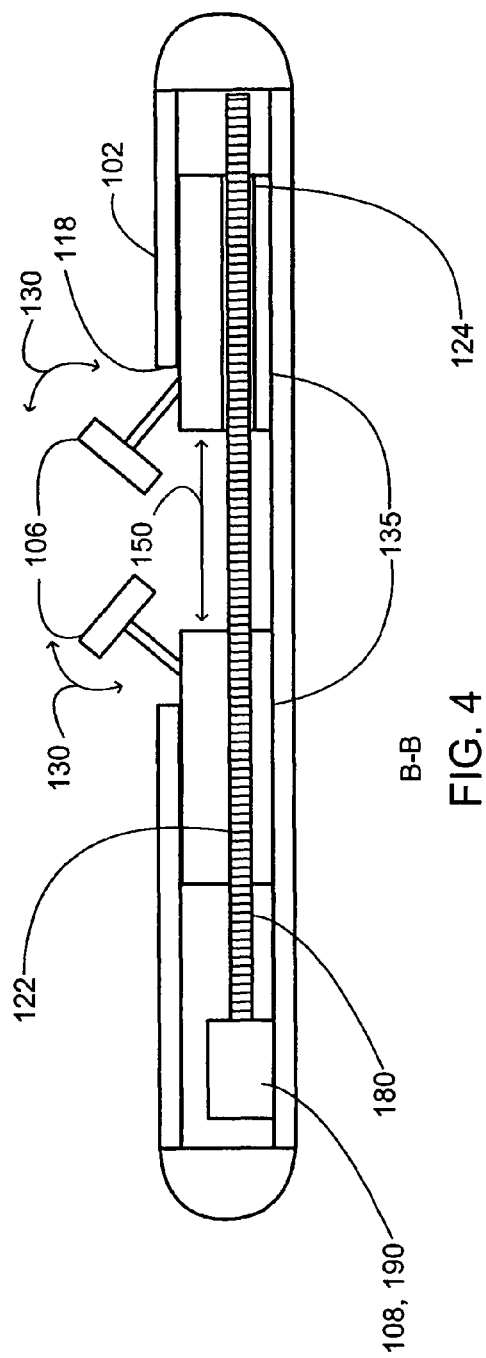
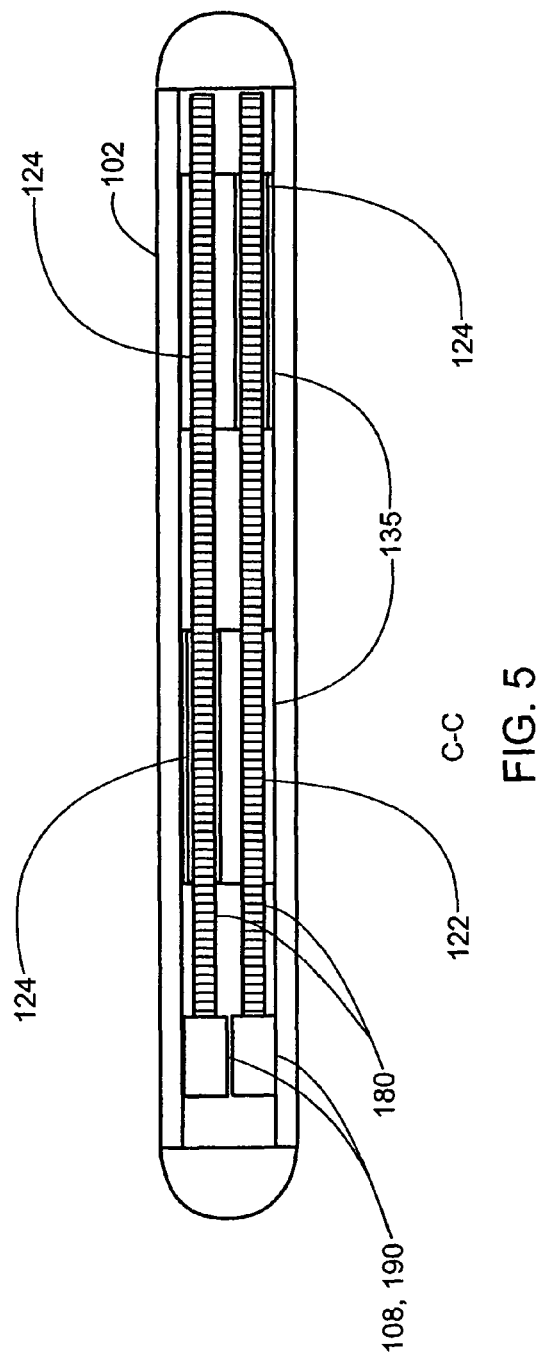

INSERTABLE DEVICE AND SYSTEM FOR MINIMAL ACCESS PROCEDURE

CROSS-REFERENCE TO RELATED APPLICATIONS

The present application is a continuation of U.S. patent application Ser. No. 10/620,298, filed on Jul. 15, 2003, now U.S. Pat. No. 7,066,879, which is expressly incorporated herein in its entirety by reference thereto.

BACKGROUND OF THE INVENTION

The present invention relates to systems and devices for use in connection with minimal or limited access procedures, such as minimally invasive surgical procedures.

Minimally invasive surgical procedures, e.g., laparascopic procedures, have dramatically reduced patient recovery times. However, the reduced recovery times have correspondingly resulted in an increase, from a surgeon's perspective, in the complexity of the surgical procedures. This is in part due to the characteristic relatively small incisions, e.g., approximately 10 mm in diameter, through which a surgeon accesses a surgical site to perform the minimally invasive surgery. The limited access adds to the complexity of the surgical procedures since surgeons must remotely manipulate sufficiently small instruments though the incisions and must also view the surgical site through the small incisions.

Imaging systems that provide a view of the surgical site for a minimal access surgical procedure typically include an endoscope, e.g., a tubular instrument containing optical lenses and light guides that feed images to an external video camera and a monitor, such as the endoscope discussed in U.S. Pat. No. 4,651,201. Endoscopes, however, have drawbacks. For instance, since the surgeon is generally using both hands to manipulate other instruments used in the procedure, e.g., forceps, scissors, coagulators/cauterizer probes, etc., an assistant is required to hold and orient the endoscope to adjust the view during the procedure. Robotics have recently been introduced to automate the task of orienting the endoscope during minimally invasive surgical procedures, such as the Automated Endoscopic System for Optimal Positioning ("AESOP"). The AESOP uses a robot arm that is directed by spoken commands to orient the endoscope. While the AESOP takes the burden off the assistant and provides a much more stable view of the field, the equipment necessary for the AESOP is complex and occupies a large part of the operating room floor.

A smaller and simpler robotic endoscope manipulator that can be placed directly over the insertion point was developed at the Institut National de Recherche en Informatique et en Automatiqueinria ("INRIA"). However, the INRIA system as well as other robotic systems fail to address the limited available range of motion about the fulcrum at the abdominal wall through which the endoscope as well as other instruments pass to gain access to the surgical site. The limited range of motion translates into limits with regard to the degree of freedom that the instruments may be oriented toward the surgical site.

Active or hyper endoscope systems have been proposed that generally consist of a multi-link robotic arm with a camera mounted thereon, such as the active endoscope discussed in Japanese Patent 2000175865, which is hereby incorporated herein by reference, which provide additional freedom with respect to orienting the endoscope camera. However, these systems require a dedicated incision for the endoscope to access the surgical site and typically require relatively high voltage to operate the actuators necessary to manipulate the hyper endoscope which from a safety perspective may be problematic when used in surgical procedures. Pill cameras have also been adopted for imaging sections of the small intestine that are out of the reach of a colonoscope, such as the pill camera described in U.S. Pat. No. 5,604,531 and U.S. Pat. No. 6,428,469. However, pill cameras do not generally include means for orienting the camera; rather, pill cameras merely rely on peristalsis to orient the camera.

There is therefore a need for systems and devices for minimal access procedures that do not require an assistant to hold and orient an instrument and that provide additional or greater freedom than is provided with an endoscope or other instrument with regard to orienting the instrument toward the site of interest. There is also a need for systems and devices for minimal access procedures that provide additional or greater freedom with regard to orienting the instrument toward a site of interest than is provided with an active or hyper endoscope that do not require a dedicated access incision into the site for the instrument.

SUMMARY OF THE INVENTION

The present invention generally provides a single or multi-functional element insertable device that can be inserted and temporarily placed or implanted into a structure having a lumen or hollow space. Once inserted into the lumen of the structure, the device is removably attached or secured to the interior of the structure, such as to the interior of a subject's abdominal wall, near a site of interest so that the functional element or elements may be oriented thereto, preferably to look down at the area of interest. The insertable and implantable aspect of the present invention obviates the limited motion about an insertion point drawback associated with endoscopes, as well as other instruments, by allowing the surgeon to move the device to different locations on the abdominal wall. Moreover, the insertable and insertable aspect allows a surgeon to insert a plurality of devices into the structure's lumen through a single incision thereby increasing access to the site with minimal incisions. Although the present invention may be described by way of example in relation to minimal invasive surgical procedures, it is understood that the invention is equally applicable to provide images, as well as various other functionality, of numerous structures with a lumen, and is therefore not limited thereto. Imaging is used herein to generally denote pertaining to producing an image of a site, such as producing a video image of a surgical site.

The present invention further provides an insertable device that has one or more functional elements configured to have or exhibit various degrees of freedom of movement with respect to orienting the functional elements. Where the functional element or element is a camera element, the device provides a wider field of view of the surgical site than that provided by standard endoscopic cameras. Additionally, the insertable device so configured provides access to a site of interest from multiple and different orientations or perspectives within the lumen, as the procedure dictates, further obviating limited mobility about the point of insertion drawback associated with endoscopes. In a multi-camera element embodiment of the invention, the imaging device provides multiple selectable views of the site and may be used in connection with a stereoscopic imaging system to provide a stereo view of the surgical site to recreate the sense of depth that is lost with a traditional video monitor.

Accordingly, in one aspect of the present invention, a device insertable into a structure having a lumen is provided that includes a first housing, at least one functional element connected to the first housing, the functional element for use during a minimal access procedure, and a securing element for removably securing the insertable device to or against a wall of a structure having a lumen. In one embodiment, the at least one functional element is movably connected to the first housing, and the device includes at least one actuating element connected to the first housing and the functional element. The actuating element is generally capable of moving the functional element in relation to the first housing in at least one degree of freedom. The securing element may be a needle protruding from the imaging device essentially inline with the elongated axis of the device, a magnet, a clamp, an adhesive, etc. In one embodiment, the insertable device is adopted for use in connection with minimal access surgical procedures. In this instance, the securing element includes a needle protruding from the insertable device essentially inline with the elongated axis of the device. The insertable device is capable therewith of being removably secured against a subject's abdominal wall by inserting the needle into tissue of the abdominal wall.

The functional elements may vary according to the desired functionality, which includes camera elements, a light elements, a laser elements, etc. In one embodiment, the functional element includes a camera element, such as a CMOS imaging sensor or a CCD image sensor. In another embodiment, the functional element is a camera element that includes a lens and a CCD image sensor mounted in a lens housing having threads therein to accept the lens and to accommodate focal adjustments.

In one embodiment, at least one functional element that is movably connected to the first housing and the device includes at least one actuating element connected to the first housing and the functional element. In this instance, the actuating element is capable of moving the camera element in relation to the first housing in at least one degree of freedom selected from a group consisting of: a first degree of rotational freedom essentially orthogonal to the elongated axis; a second degree of rotational freedom essentially inline with the elongated axis; and a third degree of translation freedom essentially inline with the elongated axis.

In another embodiment, the at least one functional element is a plurality of camera elements movably connected to the first housing and the device includes a plurality of actuating element connected to the first housing and the camera elements. In this instance, the actuating elements are capable of moving each of the camera elements in relation to the first housing in at least one degree of freedom selected from the group noted above.

In another embodiment, the at least one functional element is movably connected to the first housing and the device includes at least one actuating element connected to the first housing and the functional element. In this instance, the actuating element is capable of moving the camera element in relation to the first housing in a first degree of rotational freedom essentially orthogonal to the elongated axis allowing the functional element to be retracted into and extracted from the first housing. The actuating elements may be a motor producing rotational movement that interfaces with the functional element to translate or redirect the rotational movement produced by the motor in a direction essentially orthogonal to the elongated axis, such as with a bevel screw or worm gear assembly.

In another embodiment, the insertable device includes a second housing rotatably attached to the first housing and at least one actuating element connected to the first and second housings. In this instance, the actuating element is capable of moving the functional element in relation to the first housing in a second degree of rotational freedom essentially inline to the elongated axis by rotating the first housing in relation to the second housing.

In another embodiment, the at least one functional element is movably connected to the first housing and the device includes at least one actuating element connected to the first housing and the functional element. In this instance, the actuating element is capable of moving the functional element in relation to the first housing in a third degree of longitudinal freedom essentially inline to the elongated axis allowing the functional element to translate along the third degree of freedom.

Movement in a third degree of longitudinal freedom may be accomplished with a functional element that is mounted to a shuttle capable of moving along the elongated axis. The actuating element may be a motor producing rotational movement connected to a lead screw that interfaces with a threaded portion of the shuttle to translate the rotational movement of the motor into longitudinal movement in the shuttle along the elongated axis. Such movement may also be accomplished for a plurality of functional elements with a corresponding number of motors producing rotational movement, and a corresponding number of shuttles each functional element is mounted to a shuttle capable of moving along the elongated axis. In this instance, each shuttle includes a threaded portion and a hole, and each motor connected to a lead screw interfaces with the threaded portion of one of the shuttles to translate the rotational movement of the motor into longitudinal movement in the shuttle along the elongated axis and each lead screw passes through the hole of another shuttle to provide a guide for the other shuttle. Each shuttle may include mounted thereto at least one actuating element capable of moving the functional elements in relation to the first housing in a first degree of rotational freedom essentially orthogonal to the elongated axis allowing the functional elements to be retracted into and extracted from the first housing. In one embodiment, the plurality of actuating elements are capable of moving each of the functional elements independently of each other. The translational movement may also be accomplished with a linear rail/actuator system.

In another embodiment, the insertable device includes a second housing rotatably attached to the first housing and at least one actuating element connected to the first and second housings. In this instance, the actuating element is capable of rotating the first housing in relation to the second housing and each housing has an access opening therein capable of aligning with each other so that the first housing may be rotated to cover the functional elements and rotated to align the access openings to expose the functional element.

In another aspect of the present invention, an insertable device having an elongated axis associated therewith is provided that includes a first housing a second housing rotatably connected to the first housing, at least one camera element comprising an image sensor movably connected to the first housing, at least one actuating element connected to the first housing and the camera element, and a securing element associated with the second housing for removably securing the imaging device to or against a wall of a structure having a lumen. The actuating element is capable of moving the camera element in relation to the first housing in at least one degree of freedom selected from a group consisting of: a first degree of rotational freedom essentially orthogonal to the elongated axis, a second degree of rotational freedom essentially inline with the elongated axis, and a third degree of longitudinal freedom essentially inline with the elongated axis.

In another aspect of the invention, an insertable device having an elongated axis associated is provided that includes a first housing, a second housing rotatably connected to the first housing, a plurality of camera elements each comprising an image sensor movably connected to the first housing, at least one actuating element connected to the first housing and the second housing, the actuating element capable of rotating the first housing in relation to the second housing, at least one actuating element connected to each of the camera elements, the actuating element capable of moving the camera element in relation to the first housing in a first degree of rotational freedom essentially orthogonal to the elongated axis, and a securing element associated with the second housing for removably securing the imaging device to or against a wall of a structure with a lumen.

In another aspect of the invention, a minimal access system is provided that includes a driving device communicatively connected to at least one device insertable into a structure having a lumen, the device including at least one functional element associated therewith for use during a minimal access procedure and at least one securing element for securing the insertable device against a wall of the structure having a lumen. In one embodiment, the insertable device includes at least one actuating element capable of moving the functional element in at least one degree of freedom and the driving device provides a drive signal to remotely control the movement of the functional element.

The driving device may be adopted to provide hybrid control of the insertable device such that the driving device may autonomously control functional element movement in at least one degree of freedom. For instance, the functional element may be a camera element and the driving device may autonomously control the camera element movement to maintain a user identified object in view while the user controls camera element movement in at least one degree of freedom to obtain an image of the site of interest from different perspectives. Additionally, the at least one functional element may be a plurality of camera elements and the driving device may autonomously control the movement of the camera elements to produce a stereoscopic image of the site of interest or to create stereo images of a site of interest in real-time based on automatic vergence algorithms.

Additional aspects of the present invention will be apparent in view of the description that follows.

BRIEF DESCRIPTION OF THE FIGURES

FIG. 2 is a perspective view of an insertable device for minimal access procedures according to one embodiment of the present invention with functional elements in an extracted position;

FIG. 3 is a sectional view of an insertable device for minimal access procedures according to one embodiment of the present invention showing a functional element in an extracted position and showing the range of motion of the functional element in a direction orthogonal to the elongated axis of the device;

FIG. 4 is an sectional view of an insertable device for minimal access procedures according to one embodiment of the present invention showing functional elements each rotatably mounted onto a shuttle and a shuttle interfacing with a motor and lead screw assembly;

FIG. 5 is an sectional view of an insertable device for minimal access procedures according to one embodiment of the present invention showing shuttles each interfacing with a motor and lead screw assembly;

DETAILED DESCRIPTION OF THE INVENTION

In one aspect of the present invention, a single or multifunctional element, insertable device is provided that can be inserted and temporarily placed or implanted into a structure having a lumen or hollow space. The structure having a lumen may be the anatomical structure of a subject, such as the subject's heart, lungs, esophagus, stomach, intestines, thoracic cavity, abdominal cavity, blood vessels, etc., and non-anatomical structure, such as tanks, pipes, confined spaces, rooms, etc. In one embodiment, the present invention is adopted to be inserted and temporarily implanted into a subject's abdominal cavity to provide therewith images of a surgical site for use in connection with minimally invasive surgical procedures, such as laparascopic procedures. The subject may be any animal, including amphibians, birds, fish, mammals, and marsupials.

Figure 1:
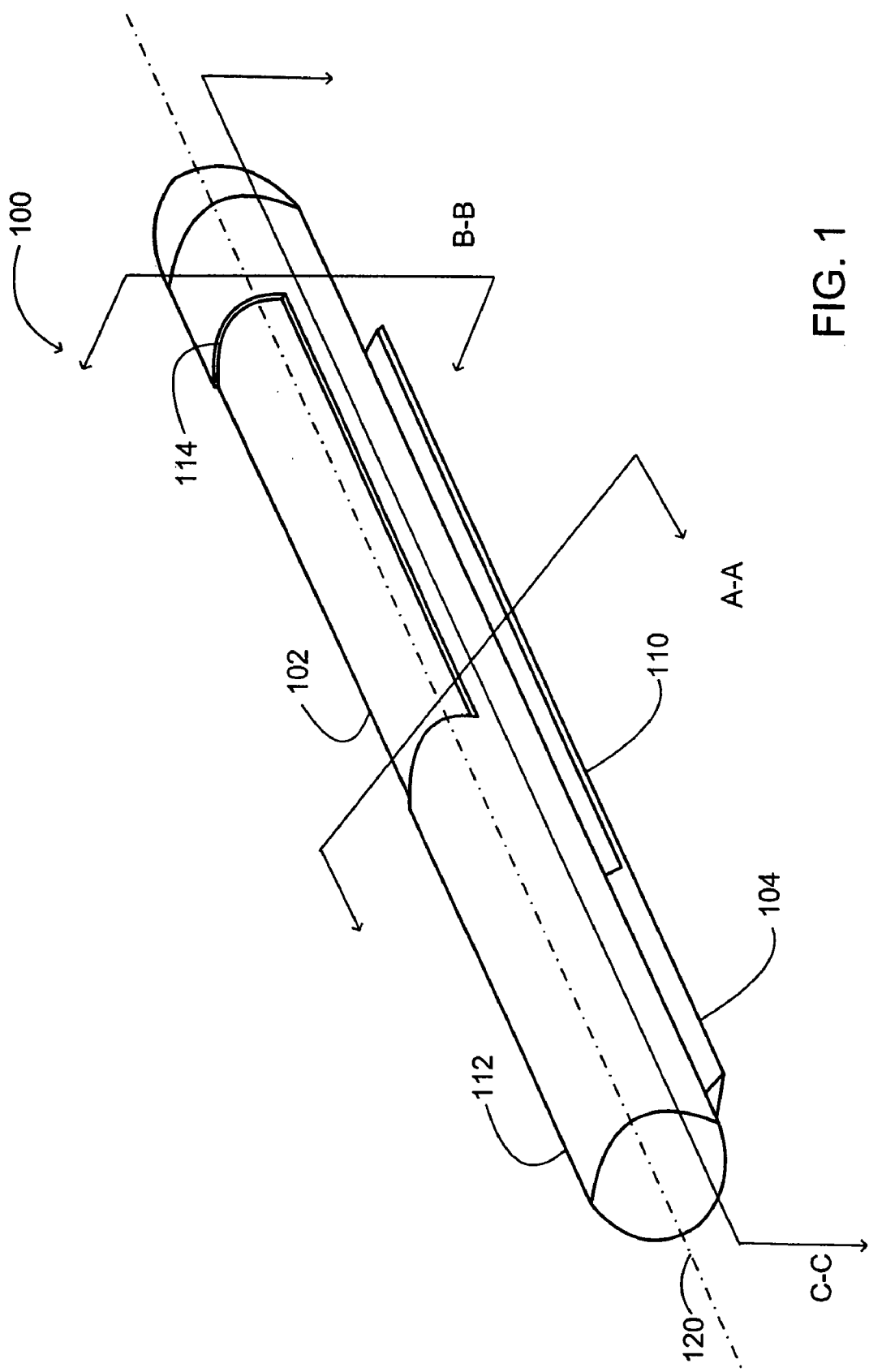
FIG. 1 is a perspective view of an insertable device for minimal access procedures according to one embodiment of the present invention functional elements in a retracted position.

Referring to FIGS. 1 and 2, the insertable device 100 of the present invention generally includes a first housing 102 and a securing element 104 for removably securing, e.g., attaching or holding, the device onto or against the wall of a structure having a lumen, at least one functional element 106 movably attached to the housing, and at least one actuating element 108 connected to the first housing for moving or causing the functional element to move in relation to the housing. A functional element is generally an instrument or device that provides a desired functionality with regard to the minimal access procedure. For instance, the functional element 106 may be a camera element, a light element, a laser element, etc. The device 100 may further include a second housing 112 movably connected to the first housing 102, which is explained in more detail below.

In one embodiment, the insertable device is adopted for surgical applications. In this instance, the securing element 104 may be a needle 110 protruding from the insertable device 100, e.g., the first or second elongated housings 102, 112, in an orientation essentially parallel to or inline with the elongated axis 120, similar to the pocket clip of a pen, such that the needle 110 may be inserted into the inner fatty tissue beneath the muscle layer of the abdominal wall to secure the device 100 to the abdominal wall. It is understood that dimensions of the needle may vary, however, the dimensions may be limited in order to limit the size of the penetration or incision created by the needle as it is inserted into the tissue and correspondingly to allow the penetration or incision to heal relatively quickly after the operation. In one embodiment, the needle 110 has a rectangular cross section and is limited to dimensions of about 1 mm by about 3 mm. The securing element 104 may alternatively be a magnet or a material attracted to a magnet, which may be used to removably secure the insertable device to the abdominal wall with corresponding magnets placed outside the body to hold the device against the abdominal wall, a clamp, an adhesive substance, etc. The type and configuration of the securing element 104 may vary depending further on the particular application for which the device is adapted.

Where the functional element 106 is a camera element, the type of camera system adapted for the insertable device 100 may vary as well, however, to facilitate use of the device for minimal access procedures, e.g., minimal access imaging, the camera system selected for the device 100 must accommodate the compact dimensions of the device 100 as dictated by the dimensions of the opening though which access into the structure with a lumen is provided. Where the device 100 is adopted for use in connection with minimally invasive surgical procedures, for instance, the dimensions of the device 100 will generally be dictated by the size of the port or trocar that provides access to the site, e.g., a port about 20 mm in diameter. A compact size with respect to the camera portion of the device 100 may be achieved, for example, with CMOS or CCD sensor chip based cameras that consist of relatively compact elements that may be located remote from each other. In one embodiment, the camera is a chip based camera with remote camera elements, such as a remote CCD image or CMOS image sensor assemblies, which allow the image sensing portion of the camera that is introduced into the surgical site to be movable in relation to the rest of camera circuitry. In another embodiment, the camera includes a 8 mm round CCD color image sensor mounted essentially perpendicular to a 17 mm long driver board, and the driver board is electrically connected to a camera control unit ("CCU") remote from the insertable device 100.

Various types and numbers of actuating elements 108 or actuators for moving the functional element in relation to the housing may be used to achieve the desired degree of freedom with regard to the movement of the functional element 106, such as piezoelectric actuators, pneumatic actuators, solenoids, shape memory alloy actuators, linear motors, motors producing rotational movement, motors producing rotational movement adopted to provide linear movement, etc. The type of actuating element 108 and the number of actuating elements 108 will vary depending on the design constraints of the insertable device 100, e.g., the dimensions as dictated by the size of the access port or opening, the degrees of freedom the functional element or elements 106 are intended to move, the number of functional element, etc. In one embodiment, at least one of the actuating elements 108 comprises a brushless DC motor producing sufficient torque to produce the desired movement in the functional element 106. The DC motor may further be connected to a lead screw which when rotated can translate a shuttle or carriage 135 in both directions along the axis of the lead screw to produce linear motion and with a bevel screw or worm gear assembly to redirect the rotational movement produced by the motor. In one embodiment, the motor runs on 6 volts, is about 27 mm long, and has a diameter of about 5 mm.

Figure 8:
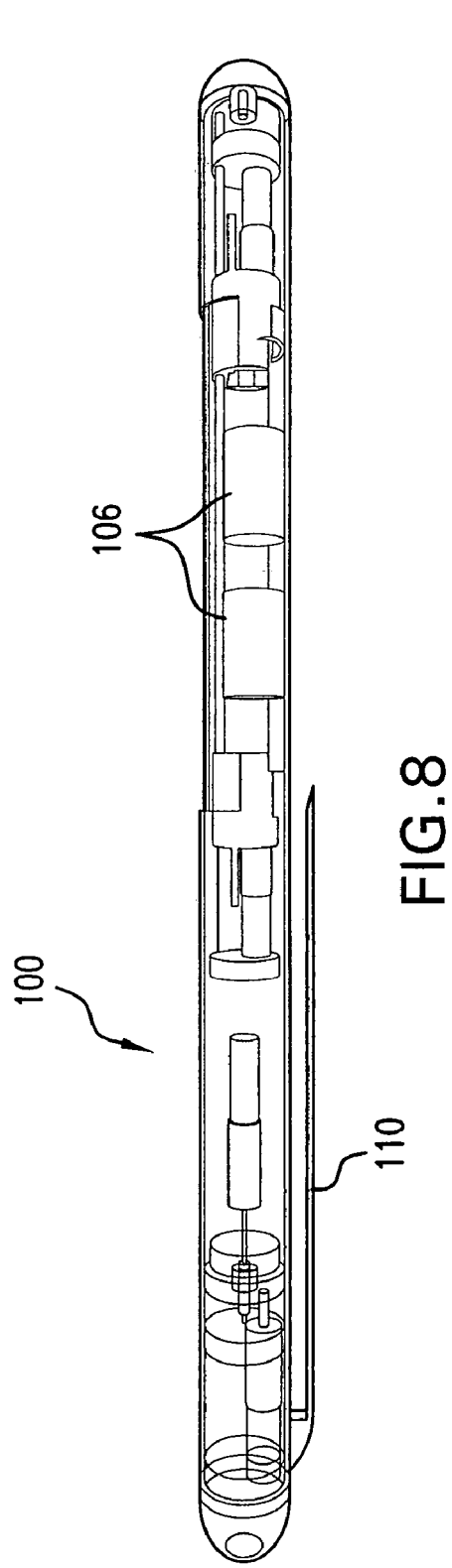
FIG. 8 is a side view of an insertable device for minimal access procedures according to one embodiment of the present invention with functional elements in a retracted position.
Figure 9:
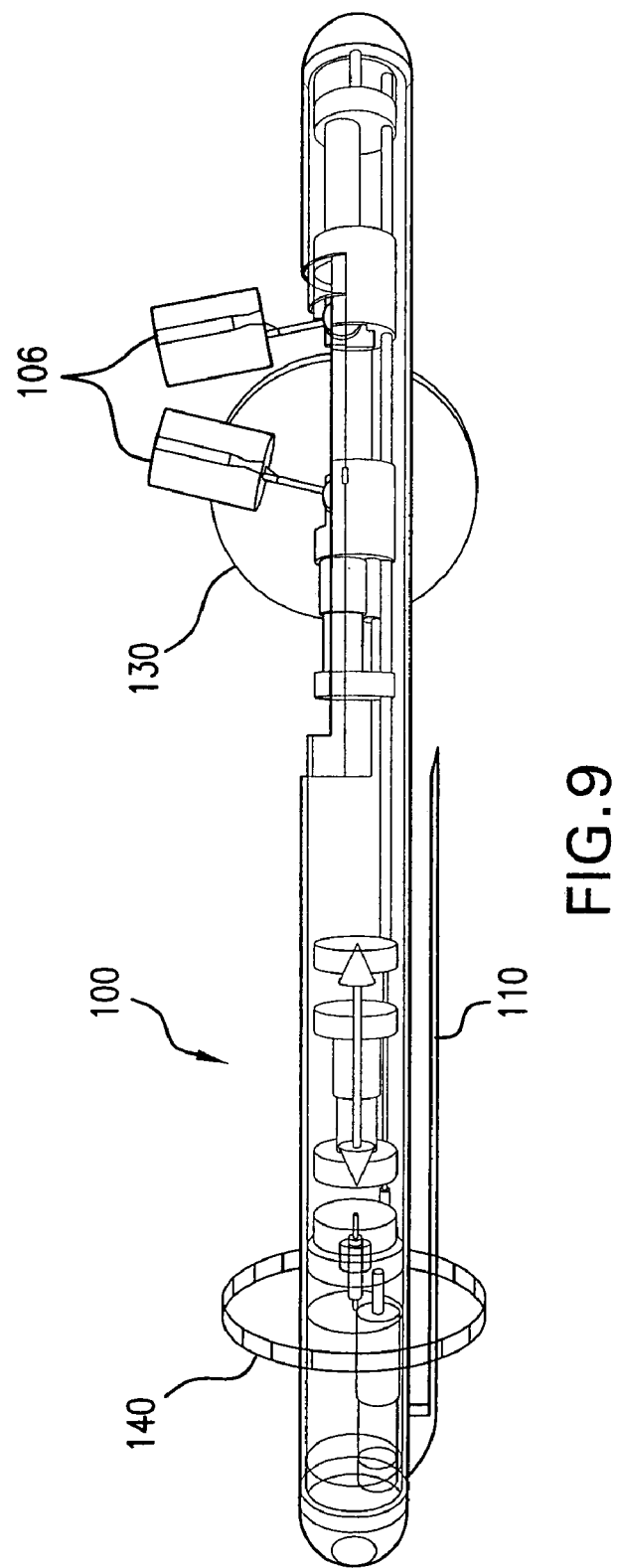
FIG. 9 is a side view of an insertable device for minimal access procedures according to one embodiment of the present invention with functional elements in an extracted position.

In at least one embodiment, the device 100 is designed to provide various degrees of freedom with regard to the movement of the one or more functional elements 106. The degrees of freedom will generally be described herein in relation to the elongated axis 120 of the device 100. The various degrees of freedom may also be described in relation to the image plane, where, for instance, panning may be viewed as a rotation, generally about a vertical axis through the image plane, tilting about a horizontal axis through the image plane, and rolling would be about the optical axis. For instance, a first degree of rotational freedom 130 essentially orthogonal to the elongated axis 120 of the device 100 which allows the element or elements 106 to be retracted into and extracted from the housing 102 and also allows the element or elements 106, e.g., the camera or cameras, to pan along the first degree of freedom 130, as shown between FIG. 8 and FIG. 9. A second degree of rotational freedom 140 essentially parallel or inline with the elongated axis 120 allows the element or elements 106 to tilt along the second degree of freedom 140. A third degree of longitudinal freedom 150 essentially parallel or inline with the elongated axis 120 allows the element or elements 106 to translate along the third degree of freedom 150. In the case of a multiple functional element device, the multiple elements 106 may be independently or simultaneously rotated and/or moved in the first and third degrees of freedom 130, 150, and in tandem in a second degree of freedom 140. This particular feature is suited, for instance, where the multiple elements 106 are camera elements for use in stereoscopic imaging. In other instances, the multiple functional elements 106 may be independent from each other and thus may be independently or stimulatingly rotated and/or moved in a first, second, and third degrees of freedom, 130, 140, 150.

The various degrees of freedom provide access to or views of the site of interest from multiple and different orientations/viewpoints. Additionally, the various degrees of freedom of movement in addition to independent control may, in a stereoscopic imaging system, provide flexibility with regard to controlling the vergence angle of the stereo pair of camera elements and establishing a baseline for stereo imaging. In one embodiment, the insertable device 100 includes five actuating elements 108, e.g., motors, which control the movement of two functional elements 106 that may be moved in the first, second, and third degrees of freedom 130, 140, 150. In one embodiment, the functional elements 106 are camera elements and the zoom and certain rotations may be accomplished in software with imaging processing capability.

Since the insertable device 100 is intended to provide functionality with respect to minimal or limited access procedures, it may be desirable to limit at least one of the overall dimensions of the device 100 to facilitate insertion into the structure with the lumen through a relatively small access opening. For example, for minimally invasive surgical procedures, an elongated tubular and/or cylindrical insertable device 100 may be configured to allow for insertion through an access port having a diameter of up to about 20 mm. Accordingly, in one embodiment, the insertable device 100 is configured to have a diameter of about 20 mm or less.

To achieve the various degrees of freedom the actuating elements 108 must generally be configured so that the actuating elements 108 fit within the dimensions of the device 100. If motors producing rotational movement, for instance, are used to provide the motive force for the functional elements 106, at least with respect to a device 100 having a diameter of about 20 mm or less, the motor will likely need to be aligned lengthwise essentially inline or parallel to the elongated axis 120 since motors typically exceed the 20 mm or less dimensional constraints of the device 100. Accordingly, motors may beneficially be used to provide rotational movement along the second degree of freedom 140, may be combined with a lead screw and shuttle arrangement to provide longitudinal movement along the third degree of freedom 150, and may be combined with a worm gear or bevel screw arrangement to provide rotational movement along the first degree of freedom 130.

In one embodiment the device 100 includes a second elongated housing 112 that is rotatably connected to the first elongated housing 102, with or without bearings, such that the first and second housings 102, 112 may be rotated in relation to each other in at least one degree of freedom. In this instance, the device 100 may be removably secured to the wall of the structure having a lumen, e.g., the abdominal wall, with the securing element that is an aspect of the second housing 112. In this instance, tilting along the second degree of freedom 140 may be achieved by rotating the first housing 102, which includes the functional element or elements 106 therein, in relation to the second housing 112. The first and second housings 102, 112 may be rotated with respect to each other with a motor that produces rotational movement appropriately connected to each of the housings 102, 112.

It is understood that the second housing 112 may occupy various portions of the length of the device 100. For instance, the second housing 112 may be long enough in relation to the elongated axis 120 to provide a sufficient bearing surface to withstand bending forces applied to the device 100 without occupying the full length of the device 100. The greatest amount of rotational freedom in the direction of the second degree of freedom 140 may be achieved in this instance if the second housing 112 does not interfere with the movement of the functional elements 106 while the elements 106 are in an extracted position. The second housing 112 may occupy a greater portion of the length of the device 100 to provide a protective cover for the functional elements 106. In this instance, the second housing 112 will include an access opening 114 capable of aligning with an access opening 118 of the first housing 102 so that second housing 112 will cover functional elements 106 retracted within the first housing 102 for insertion into the structure and, once inserted or removably secured to the structure, the first housing 102 may be rotated, e.g., 180 degrees, to reveal the functional elements 106 though the access openings 114. The access opening 118 of the first housing 102 may further allow the functional element or elements 106 to retract into and extract from the first housing 102. In one embodiment, the access openings 114, 118 of the first and second housings 102, 112 are sized to allow the maximum amount of rotational movement along the second degree of freedom 140, e.g., the access opening 114 of the second housing 112 is dimensionally equal to or greater circumferentially than the access opening 118 of the first housing 102, as shown in FIG. 3. In one embodiment, the first and second housing are capable of being rotated at least 270 degrees with respect to each other when the functional elements 106 are in a retracted position and/or at least 180 degrees with the functional elements 106 extracted.

In one embodiment, the longitudinal movement in the direction of the third degree of freedom 150 is produced by mounting at least one functional element 106 onto a shuttle 135 that is capable of moving along the elongated axis 120 within the lumen of the first housing 102. Each shuttle 135 further includes an actuating element 108 associated therewith for producing the longitudinal movement within the first housing 102. Referring to FIGS. 4 and 5, in one embodiment, the shuttle 135 is moved along the elongated axis 120 within the first housing 102 by a motor 190 connected to a lead screw 180 that interfaces with a threaded portion 122 of the shuttle 135. Accordingly, the shuttle 135 moves within the first housing 102 as the lead screw 180 is screwed and unscrewed in relation to the shuttle 135. A track or guide may be provided within the first housing 102 and a corresponding key in the shuttle 135 to restrict undesirable rotation of the shuttle 135. A second shuttle 135 with a threaded portion 122 having threads in a reverse direction than that the first shuttle 135 may interface with the lead screw 180 with corresponding reverse threads to move the shuttles 135 within the first housing 102 in directions to and from each other. In one embodiment, independent longitudinal movement for each of the shuttles 135 is achieved with a motor 190 and lead screw 180 combination for each of the shuttles 135. Rotational movement for each shuttle 135 may be restricted with a guide and key arrangement as noted above, or, alternatively, with each other's lead screw. In this instance, each shuttle 135 includes a threaded portion 122 that interfaces with one lead screw 180 connected to a respective motor 190 associated with the shuttle and one hole 124 larger than the threads of the lead screw 180 connected to the motor 190 associated with the other shuttle 135 which allows the shuttles to use each other's lead screw 180 as a guide.

Figure 6:
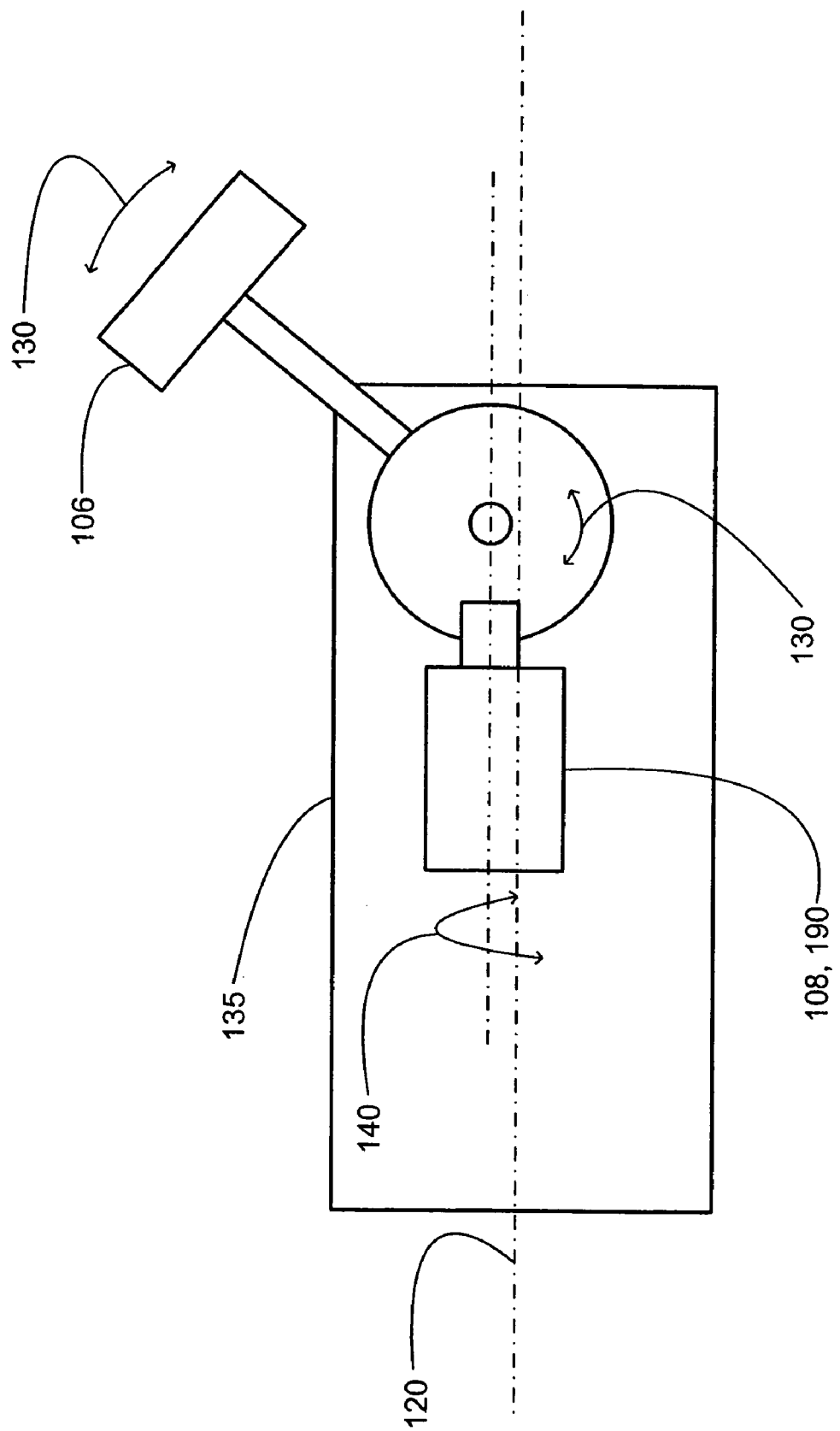
FIG. 6 is a perspective view of a shuttle with a functional element rotatably mounted thereon and the functional element interfacing with a motor with a worm gear assembly.

Rotational movement in the direction of the first degree of freedom 130 is achieved with an actuation element 108 that engages the functional element 106 to retract and extract the functional elements into and out of the device 100. In one embodiment, the actuation element 108 is a motor 190 that interfaces with functional element 106 with a worm gear assembly to redirect the rotation produced by the motor 190 in a direction essentially orthogonal or essentially perpendicular to the axis of the motor 190 or the elongated axis 120, as shown in FIG. 6. In one embodiment, the functional elements 106 are mounted to the shuttles 135 so that maximum freedom in the direction of the third degree of freedom 150 is achieved, e.g., in a manner such that the functional elements appear to face each other. In one embodiment, the distance between the functional elements 106 or shuttles is up to 10 mm.

In one embodiment, at least one of the functional elements 106 is a camera element and the shuttle 135 includes a camera element rotatably attached thereto which includes an image sensor, such as a CCD or CMOS image sensor, mounted in a lens housing that has threads therein to accept a lens with matching threads which accommodates focal adjustments. In one embodiment, a CCD sensor and lens are mounted on a pedestal, which is rotatably connected to the shuttle 135 so that the pedestal may tilt about an axis that is orthogonal to the shuttle motor. The driver board mounted on the shuttle 135 may be connected to the CCD image sensor with or without a flexible ribbon cable.

It is understood that the various components of the device 100 may be manufactured from a variety and/or a combination of biocompatible and non-biocompatible materials, such as polyester, Gortex, polytetrafluoroethyline (PTFE), polyethelene, polypropylene, polyurethane, silicon, steel, stainless steel, titanium, Nitinol, or other shape memory alloys, copper, silver, gold, platinum, Kevlar fiber, carbon fiber, etc. Where non-biocompatible materials may come into contact with anatomic structure, the components made from the non-biocompatible materials may be covered or coated with a biocompatible material. In one embodiment, the housings 102, 112 of the device 100 are manufactured from stainless steel. The housings may be stainless steel tubes of various diameters. In one embodiment, the second housing 112 has a diameter of about 5 mm (0.197") to about 25 mm (0.984"), and is about 127 mm (5") to about 228 mm (9") long. In one embodiment the second housing has a diameter or of 9/16" and is about 7.8" long. In another embodiment, the device has a wall thickness of 0.028". The device may further have spherical end caps to ease insertion into the structure. An about 50 mm (2") to about 152 mm (6") long section of the second housing 112 may be cut away to produce an access opening 114 which allows the functional elements 106 to tilt when extracted. In on embodiment, the access opening is about 2.6" long. In one embodiment, the first housing 102 has a 0.028" thickness. In another embodiment, the first housing has a smaller diameter than the second housing which is also between about 5 mm to 25 mm and a length of about 127 mm to about 228 mm. In one embodiment, the first housing has a ½" diameter and is 6" long. A portion of the first housing 102 is cut away to produce an access opening 118 to allow the cameras to be retracted therein and extracted therefrom. The first housing 102 preferably includes sufficient space to house cable to provide sufficient slack to accommodate the movement of the functional elements 106 as described herein.

It is understood that the device 100 may be adopted to provide additional functionality. For instance, the functional element 106 may be an instrument, such as a light for illuminating the site of interest, a laser for cauterizing, coagulating, ablation, a scissors ultrasonic dissector, a dissecting instrument, a needle, a grasper, a scalpel, diathermy/cautery instruments, or any other type of surgical instrument. The instrument may be fixed in relation to the device or may be moveably in relation to the device in one of the various degrees of freedom, as noted above. Moreover, the device may include multiple functional elements 106, such as at least two of a light, laser, and a camera element. The light may also be fixed to any one of the housing or incorporated into the camera element. In one embodiment, the multiple instruments may be controlled consistently with each other. For example, a light may be controlled in the various degrees of freedom to illuminate the site consistent with the movement of the camera element. In one embodiment, the insertable device 100 includes a plurality of shuttles 135, one shuttle 100 including a camera element and at least one shuttle 135 which includes a functional element, such as a light, a laser, etc., thereon.

Figure 7:
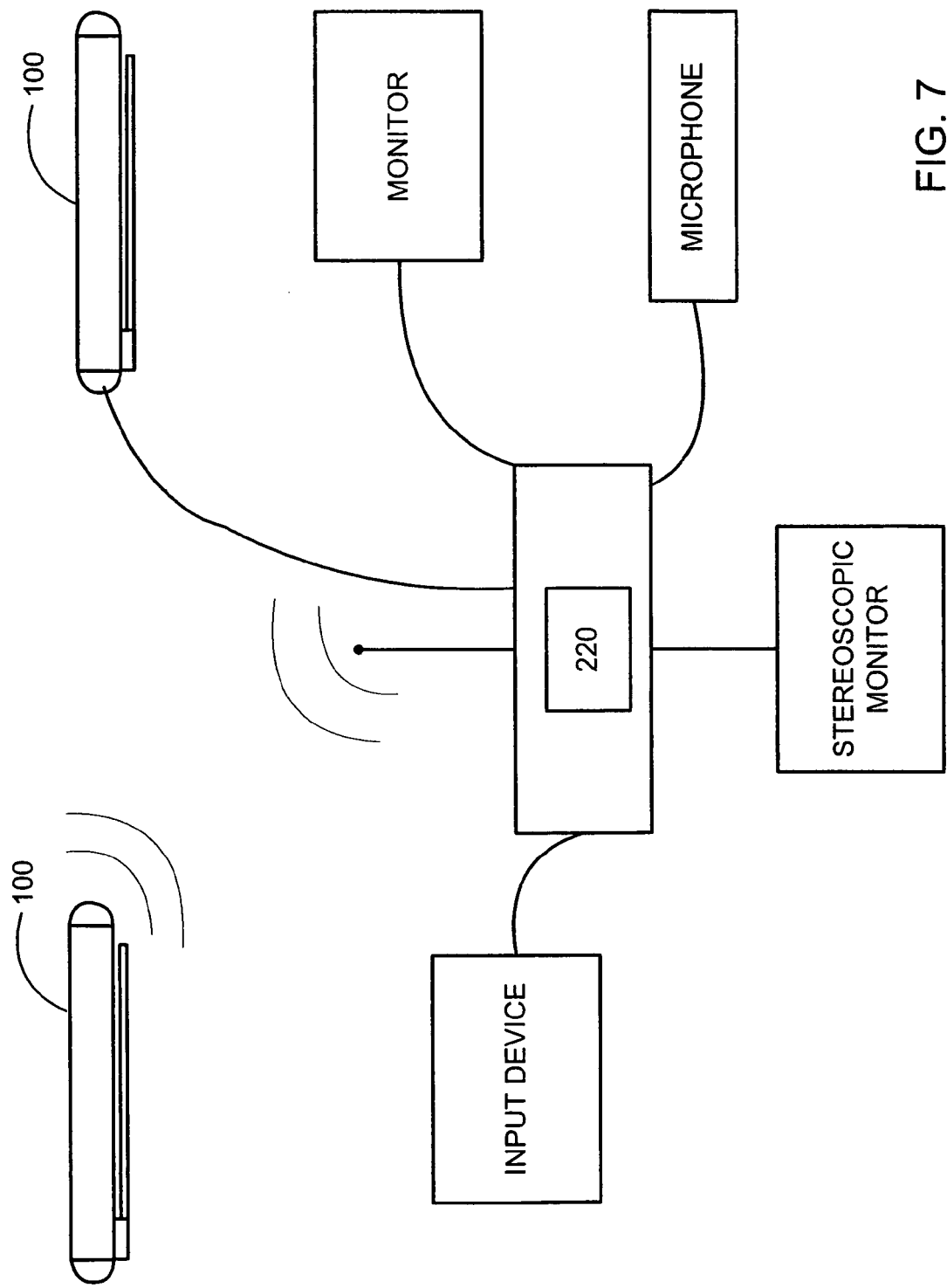
FIG. 7 is a diagram of a minimal access system according to one embodiment of the present invention.

Referring to FIG. 7, a minimal access system, according to one embodiment, includes at least one insertable device 100 and a driving device 202. The driving device 202 is generally a device, which provides the driving signal to produce the desired functionality to the insertable device 100, such as movement in the relevant degrees of freedom of motion, imaging, power, energy for cauterizing, coagulation, ablation, etc. In one embodiment, the driving device 202 includes at least one controller 204 to drive at least one motor associated with the device 100 and to reproduce the images of the site of interest. In one embodiment, the system includes a plurality of insertable devices 100 communicatively connected to the driving device with each of the devices 100 providing a different functionality, such as one of imaging, light, ablation, coagulation, and ablation.

In one embodiment, the system provides hybrid control, which allows the user to control movement with regard to some of the degrees of freedom of the device while the system autonomously controls movement with regard to the remaining degrees of freedom. For example, the system may be adopted to autonomously control camera movement in the first and second degrees of freedom 130, 140 in order to keep a user-identified object in view, while the user controls camera movement along the third degree of freedom to provide images from different orientations/perspectives. In one embodiment, the autonomous system maintains the user identified object, such as an organ, in view while the user orients at least one camera element. This may be accomplished with a constraint-based sensor planning system that can associate viewpoints of modeled objects. The planning system generally incorporates constraints on viewpoint visibility, depth-of-field, and image resolution to plan correct viewing parameters and positions. This aspect is particularly beneficial when multiple camera insertable devices are in use that provide surgeons with a choice of potential viewpoints and to provide stereoscopic imaging.

The system may further be adopted to perform open loop position control of the one or two functional elements in the relevant degrees of freedom, interface the open loop control to the surgeon through either voice activation or an input device, produce a video image of the site, track moving structures within the body, and/or create stereo images in real-time based on automatic vergence algorithms.

The driving device 202 generally provides control remote from the insertable device 100, e.g., the driving device 202 is located exterior to the body whereas the insertable device 100 may be implanted to provide the relevant functionality with respect to minimal access procedures. The driving device 202 may interface with the device 100 with cables, such as a cable 2 m long and 1-12 mm in diameter. The cable generally comprises a plurality of wires that carry power, energy, video, and/or the drive signal to control the elements of the device 100. Alternatively, the video and/or the drive signal may be wirelessly transmitted to the device to reduce the number of wires necessary to operate the device 100. Power may also be provided with a battery within the driving device 100 to eliminate cabling altogether. For extended use the battery may be charged or maintained with wireless energy transducers.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A device insertable into a bodily lumen, comprising:
   a first housing having an aperture and completely insertable within the bodily lumen;
   a second housing rotatably attached to and at least partially surrounding the first housing;
   a securing element adapted to removably secure the first housing entirely within the bodily lumen;
   a functional element movably connected to the first housing; and
   an actuator connected to and situated entirely within the first housing and adapted to move the functional element in relation to the first housing;
   wherein at least one of: (i) the functional element is movable through the aperture between a first position inside the first housing and a second position at least partially outside the first housing; and (ii) an entirety of the functional element is movable inside the first housing along a longitudinal axis of the first housing.

2. The device according to claim 1, wherein the functional element includes an imaging device.

3. The device according to claim 1, wherein the functional element includes at least one of a camera, a laser, a light element, a scissor ultrasonic dissector, a dissecting instrument, a needle, a grasper, a scalpel, and a diathermy/cautery instrument.

4. The device according to claim 1, wherein the functional element includes a camera which includes a lens and a sensor mounted in a lens housing having threads therein adapted to receive the lens and to accommodate focal adjustments.

5. The device according to claim 1, wherein the functional element includes at least one of a CMOS imaging sensor and a CCD imaging sensor.

6. The device according to claim 1, wherein the securing element includes at least one of a magnet, a clamp, and a needle.

7. The device according to claim 1, wherein the functional element is rotatable along the longitudinal axis of the device.

8. The device according to claim 1, wherein the aperture is openable and closeable.

9. The device according to claim 1, wherein the second housing has an aperture.

10. The device according to claim 1, wherein the functional element is controllable from outside the bodily lumen while the housing of the device is completely contained within the bodily lumen.

11. The device according to claim 1, wherein the securing element is fixed in place relative to the first housing.

12. The device according to claim 1, wherein the device is adapted to be completely inserted into the bodily lumen.

13. A device insertable into a structure having a lumen, comprising:
- a first housing completely insertable within the lumen;
- a second housing completely insertable within the lumen along with the first housing and rotatably connected to the first housing;
- a functional element movably connected to at least one of the first housing and the second housing;
- at least one first actuator connected to and situated within at least one of the first housing and the second housing adapted to rotate the first housing and the second housing in relation to each other;
- at least one second actuator connected to the at least one functional element and connected to and situated within at least one of the first housing and the second housing, and adapted to move the functional element in relation to at least one of the first housing and the second housing; and
- a securing element associated with at least one of the first housing and the second housing adapted to removably secure the device inside the structure.

14. The device according to claim 13, wherein the functional element includes an imaging device.

15. The device according to claim 13, wherein the at least one second actuator is adapted to move the functional element into and out of an aperture in each of the first housing and second housing when these apertures are aligned by the one first actuator.

16. The device according to claim 13, wherein the device is adapted to be completely inserted into the lumen.

* * * * *